(12) United States Patent
Stollman (10) Patent No.: US 12,354,725 B2
(45) Date of Patent: *Jul. 8, 2025

(54) GAMIFICATION SYSTEMS AND METHODS FOR IMPROVED HEALTHCARE OUTCOMES

(71) Applicant: Jeff Stollman, Wayne, PA (US)

(72) Inventor: Jeff Stollman, Wayne, PA (US)

(*) Notice: Subject to any disclaimer, the term of this patent is extended or adjusted under 35 U.S.C. 154(b) by 397 days.

This patent is subject to a terminal disclaimer.

(21) Appl. No.: 17/586,070

(22) Filed: Jan. 27, 2022

(65) Prior Publication Data

US 2022/0148698 A1 May 12, 2022

Related U.S. Application Data

(63) Continuation of application No. 15/740,851, filed on Dec. 29, 2017, now Pat. No. 11,238,969.

(51) Int. Cl.
| | | |
|---|---|---|
| *G16H 20/13* | (2018.01) | |
| *A61B 5/02* | (2006.01) | |
| *A61J 1/00* | (2023.01) | |
| *A61J 1/03* | (2023.01) | |
| *A61J 7/04* | (2006.01) | |
| *A63F 13/335* | (2014.01) | |
| *A63F 13/44* | (2014.01) | |
| *A63F 13/46* | (2014.01) | |
| *A63F 13/80* | (2014.01) | |

(Continued)

(52) U.S. Cl.
CPC ............ *G16H 20/13* (2018.01); *A61B 5/02* (2013.01); *A61J 1/00* (2013.01); *A61J 1/03* (2013.01); *A61J 7/0436* (2015.05); *A61J 7/0445* (2015.05); *A63F 13/335* (2014.09); *A63F 13/44* (2014.09); *A63F 13/46* (2014.09); *A63F 13/80* (2014.09); *G16H 10/60* (2018.01); *G16H 40/67* (2018.01)

(58) Field of Classification Search
CPC A63F 13/46; A61J 7/0436; A61J 1/00; G16H 10/60; A61B 5/02
See application file for complete search history.

(56) References Cited

U.S. PATENT DOCUMENTS

| | | | | |
|---|---|---|---|---|
| 8,799,020 | B2 * | 8/2014 | Roberts | G16H 20/10 705/2 |
| 2007/0272583 | A1 * | 11/2007 | Kulkarni | G07F 17/0092 705/3 |

(Continued)

*Primary Examiner* — Jay M. Patel (57) ABSTRACT

A gamified pharmaceutical packaging, dispensing system, and methodology is disclosed. The innovative gamified smart packaging system and methodology provides a variety of incentives to patients and relevant teams to take their medications, on time, and at the correct dosage. The system comprises monitored pharmaceutical dispensing devices that communicate with a plurality of compute devices, or smartphones. Each time the patient dispenses the medicine from the dispensing device, a signal is transmitted to the compute device. Upon receiving the signal, the compute device records the dispensing event, calculates a specific "score" for that event, and reports the patient's cumulative "score" of successfully dispensing the medicine. If a dispensing event signal is not received in a timely fashion, the system sends a prompt to the patient to take their medication. Accumulating points by properly taking the prescribed medication allows the patient and/or team to be eligible to receive various benefits.

23 Claims, 3 Drawing Sheets

(51) Int. Cl.
*G16H 10/60* (2018.01)
*G16H 40/67* (2018.01)

(56) References Cited

U.S. PATENT DOCUMENTS

| | | | | |
|---|---|---|---|---|
| 2013/0332194 | A1* | 12/2013 | D'Auria | G16H 10/60 |
| | | | | 705/3 |
| 2014/0100867 | A1* | 4/2014 | York | G06Q 30/0207 |
| | | | | 705/2 |
| 2014/0156308 | A1* | 6/2014 | Ohnemus | G16H 40/67 |
| | | | | 705/3 |
| 2016/0063204 | A1* | 3/2016 | Srinivasan | G16H 10/60 |
| | | | | 705/2 |
| 2017/0326033 | A1* | 11/2017 | Kraft | G16H 40/67 |
| 2018/0049675 | A1* | 2/2018 | Kerber | A61B 5/1112 |
| 2018/0240140 | A1* | 8/2018 | Whitley | G06Q 50/22 |

\* cited by examiner

GAMIFICATION SYSTEMS AND METHODS FOR IMPROVED HEALTHCARE OUTCOMES

CLAIM OF PRIORITY

This application claims the benefit of priority under 35 U.S.C. § 119(e) from U.S. patent application Ser. No. 15/740,851, filed on 29 Dec. 2017, now allowed, and the contents of which are incorporated by reference herein in its entirety as if set forth in full.

FIELD OF THE INVENTION

The present invention generally relates to the field of dispensing patient pharmaceuticals and, more specifically, relates to systems, methods, and processes used for incentivizing patients to take their medications on a timely basis, and at the correct dosage. In further particularity, the gamified smart packaging system is designed to provide a variety of incentives to patients or relevant teams, including teams of patients, or patients and caregivers, or patients and relevant third parties, to ensure the patients take their medicines, on time, and at the correct dosage.

The system comprises monitored pharmaceutical dispensing devices, or smart packaging, that are in communication with at least one compute device, such as a smartphone and/or a remote server. Each time the patient dispenses the medicine from the dispensing device or smart package, the device transmits a signal to the compute device. Upon receiving the signal, a software routine operating on the compute device, which may be an app operating on a smart phone, records the dispensing event, including the time of the dispensing event, calculates a specific "score" for that event, and then reports the patient's specific score and possibly a cumulative "score" of successfully dispensing the medicine. In some embodiments, a local compute device may transmit the recording of the dispensing event, and possibly a calculated specific score to a remote server for additional analytics and processing. The reporting of a current or cumulative score could be made to the patient solely, or also, with permission, to a physician and/or other team members. If a dispensing event signal is not received in a timely fashion, the app or system sends a prompt to the patient as a reminder to take his or her medication. Accumulating points by properly taking the prescribed medication provides a basis for the patient to be eligible to receive various benefits, such as the ability to play an on-line game or to further compete for sponsored benefits.

BACKGROUND DESCRIPTION OF THE SYSTEMS AND METHODOLOGIES

It is well recognized that the failure to properly take prescribed medication, either by not taking the medication, not taking it at the correct time or dosage (which could entail taking either too little or too much of the medication), is a very real problem both in the United States and internationally. According to an article published in the Annals of Internal Medicine, U.S. citizens fail to comply with medication prescription protocols for a variety of reasons, including failure to understand the protocol, belief that the patient no longer needs the medication, or simply being forgetful. International pharmaceutical users likely experience the same medication adherence issues.

In the U.S. alone, non-compliance with prescription protocols costs anywhere between $100 billion to $289 billion annually. Moreover, in the U.S., it is estimated that approximately 50 percent of all medications for chronic disease are not properly taken by patients or the prescribed protocol is not followed. Various studies further estimate that failure to follow prescription protocols causes approximately 125,000 deaths each year, and up to 10 percent of all emergency hospitalizations. Furthermore, during clinical trials of new drugs where every data point is valuable, the inability of patients to take their medications in a timely fashion may disqualify the results for that patient and in turn delay the approval of effective medication.

For many ailments for which medication is prescribed, symptom relief is usually a sufficient enough incentive for the patients to take their medication in a timely fashion. But many other ailments and maladies exist for which there are either no recognizable symptoms—especially those associated with lifestyle choice, either past or present—or where the symptom relief is achieved only over an extended period of time. For such ailments, the lack of a near term symptom-reduction benefit significantly reduces the patient's incentive to continue taking medications at the prescribed intervals and doses.

Various prior devices, systems and methodologies have been created to attempt to effectively address this issue of an incentive-based pharmaceutical drug adherence program or protocol. Patents and patent applications exist for such incentive-based systems, as well as for smart, or intelligent, dispensing systems. The following provides an overview of some of the known prior patents and applications.

Incentive Systems for Medication Adherence

Heath et al., U.S. Pat. No. 8,508,346, System And Method For Automating And Verifying Medication Compliance (Heath), discloses a reward system linked to a smart dispenser. The Heath system receives from a remote processor alerts of medications to be taken and reads from the dispenser whether dispensing has occurred, and presents a message to the user of the compliance results. The system displays a reward for the patient when the patient complies with the instructions. There is no description of the type of "rewards" that may be given, and there is no disclosure of incorporation of any teams or competitive gamification.

Bartholomew, III et al., US 2012/0245960, Points-Based Reward Program For Improving Medication Adherence And Outcomes (Bartholomew), describes a "frequent flyer" type of program for medication users. A patient registers with a website and receives points that can be used for various merchandise/services. The website and not the pharmaceutical package sends a reminder to take the medication as well as refill reminders to the patient via phone, email, or SMS. Points can also be earned from participation in various educations activities, and also by achieving particular lab values. In Bartholomew there is no disclosure or suggestion of gamification using team members, or involving doctors or other caregivers.

De Oliveira et al., U.S. Pat. No. 8,439,758, Medication Compliance Using Persuasive Computing (De Oliveira), awards points for taking medication. The points can be applied to various rewards. Points received are based on the time difference of taking a medication and the scheduled dose time. Timing information is received from the opening of a pillbox that has a smart lid that communicates with a local computing device (e.g., a smartphone) which uploads the information to a server. The De Oliveira system includes the use of competition and a chat feature for competitors to remind each other to take their medications. Patients receive points for reminding others to take their medications. There is no disclosure in De Oliveira relating to the use or structure of teams.

Filipi et al., US 2014/0219064, Medical apparatus for data storage (Filipi), focuses on a smart watch as a notification system. The specification describes a gaming functionality, such as one assigning points to a patient based upon compliance, which may be used to encourage greater compliance and/or foster competition between patients. Prizes may also be selected or awarded to a patient based upon the assigned points. As with the above patents and applications, in Filipi there is no disclosure identifying the use of teams of patients or other caregivers.

Smart Dispensing Technology

A relevant good example of the innovative use of smart dispensing technology for pills is provided by Nguyen, US 2010/0076595, Smart pill dispenser (Nguyen). This hardware disclosure is to a pill dispenser capable of (1) tracking prescription information, (2) an alert mechanism to prompt the user to take his or her pills, (3) a sensor to detect the time a pill has been removed, (4) automatically track the number of pills in the dispenser, (5) control the number of pills being dispensed, (6) linking with other dispensers, and (7) a communication link. The two-way communications link can inform a doctor, transmit data from other sensors (e.g., sensors for blood glucose, heart rate, etc.), or receive prescription modifications from the doctor. The system also describes the receipt of a notice of an upcoming appointment, as well as to interact with any insurer or pharmacy. Similar to the above patents and applications, there does not appear to be any disclosure or suggest of using gamification and collaboration features.

Kulkarni, U.S. Pat. No. 7,877,268, Intelligent Box, discloses a smart pill box that tracks the weight of its contents to account for when medications have been taken. Specifically, it records the timing of a change in weight. It includes a "disease management system" to prompt the user to take his medications. It also includes a communication system that may be a "telephone line to external systems to store the information of the patient's compliance," and thus can be used to alert a doctor or nurse of non-compliance. The user is prompted to take his or her medicine for the appropriate vial in the pill box by an audio alarm that indicates time to take medicine and an LED indicated which vial should be removed from the box to take the pill. Similar to the above patents and applications, there does not appear to be any disclosure or suggest of using gamification and collaboration features.

Brue, U.S. Pat. No. 7,158,011, Medication Compliance Device (Brue), targets dispensing of multiple medications and teaches a portable, multi-compartment box with containers for different medications along with a microprocessor that can be programmed to set off an alarm and open at various time intervals. The device further includes a communications port for uploading compliance data and downloading of information. As with most of the other noted art, there does not appear to be any disclosure or suggest of using gamification and collaboration features.

Hanpeter, et al., U.S. Pat. No. 4,616,316, Medication compliance monitoring device having conductive traces upon a frangible backing of a medication compartment (Hanpeter), discloses use of smart pill bottle technology and applies such technology to blister-pack medications. Hanpeter teaches a blister pack with conductive traces that connect to an electronic memory circuit. The electronic memory circuit detects the ruptures and stores the time data thereof over said extended period of time. During the patient's follow-up visit a microcomputer is employed to retrieve the dose-removal-time data from the memory circuit. There is no gamification or incentive protocols suggested or described in the Hanpeter patent.

Czaja et al., US20140277705, Medication Compliance Monitor—Method and Apparatus (Czaja), further describes use of escalation as a means to prevent dispensing. In Czaja, a medication dispenser wirelessly connects to an app. The app authenticates the user, and provides features of scheduling and alerting (through audio or text messaging) for the user and a third party (in the case of non-compliance). The dispenser detects dispensing by weight and can prevent dispensing. Again, there is no gamification or incentive protocols suggested or described in this application.

The known and currently existing pharmaceutical incentive systems and methodologies described above, and otherwise, do not fully address the primary problems and issues of patients not complying with prescription drug protocols. Accordingly, there is a need for a comprehensive, automatic, incentive-based system and method to monitor patients' adherence to medication protocols, and to incentivize compliance with such protocols during the entire prescription duration, and thereby address the problem of patients' non-adherence to prescription regimens.

SUMMARY OF THE INVENTION

The present invention overcomes the disadvantages of the prior art and fulfills the needs described above by providing automatic incentive-based systems and methods to monitor a patient's adherence to medication protocols, and to incentivize the patient to adhere to the medication protocols for the entire prescription duration.

A preferred embodiment of the invention is a computerized system for incentivizing patient compliance with prescription pharmaceutical protocols, said system comprising (a) a plurality of smart pharmaceutical packages, each said smart pharmaceutical packages capable of identifying when each pharmaceutical has been dispensed, and capable of transmitting a signal upon the occurrence of each such dispensing event; (b) at least one compute device having a real-time communications link with said plurality of smart pharmaceutical packages; and (c) a computerized methodology operating within said at least one compute device; wherein said computerized methodology comprises the steps:
  (1) loading onto said at least one compute device, a prescription pharmaceutical protocol, said protocol having an indication of pharmaceutical dosage and related timing for said dosage;
  (2) commencing a timeline for compliance monitoring for said pharmaceutical protocol;
  (3) monitoring date and time as compared to said pharmaceutical protocol;
  (4) identifying each dispensing occurrence from each of said plurality of smart pharmaceutical packages;
  (5) transmitting a signal from said plurality of smart pharmaceutical packages to at least one of said at least one compute devices of a dispensing occurrence;
  (6) recording by said at least one compute device said dispensing occurrence including the date and time of such occurrence;
  (7) calculating a current score based upon said dispensing occurrence;
  (8) accumulating said score with prior calculated scores;

(9) transmitting said current score and accumulated score to at least one of said at least one compute device to report the occurrence of said dispensing event and said achieving of said calculated current score;
(10) if a time period lapses without receiving a transmission from said plurality of smart pharmaceutical packages of a dispensing occurrence, then identifying a noncompliance event;
(11) recording said non-compliance event; and
(12) transmitting a signal to said at least one compute device of said non-compliance event to urge and incentivize compliance with said prescription pharmaceutical protocol.

Another preferred embodiment of the invention is a computerized methodology for incentivizing patient compliance with prescription pharmaceutical protocols, using a plurality of smart pharmaceutical packages in communication with at least one compute device operating the methodology, wherein the methodology comprises the steps:
(1) loading a prescription pharmaceutical protocol onto said at least one compute device, said protocol having an indication of pharmaceutical dosage and related timing for such dosage;
(2) commencing a timeline for compliance monitoring for said pharmaceutical protocol;
(3) monitoring date and time as compared to said pharmaceutical protocol;
(4) identifying a transmission from said plurality of smart pharmaceutical packages of an application, dispensing, injection, ingestion, or in-body detection occurrence;
(5) recording said application, dispensing, injection, ingestion, or in-body detection occurrence including the date and time of such occurrence;
(6) calculating a current score based upon said dispensing occurrence;
(7) accumulating said current score with prior calculated scores;
(8) transmitting said current score and accumulated score to at least said at least one compute device to report the occurrence of said dispensing event and said achieving of said calculated score;
(9) if a time period lapses without receiving a transmission from said plurality of smart pharmaceutical packages of a dispensing occurrence, then identifying a noncompliance event;
(10) recording said non-compliance event; and
(11) transmitting a signal to said at least one compute device of said non-compliance event to urge and incentivize compliance with said prescription pharmaceutical protocol.

BRIEF DESCRIPTION OF THE DRAWINGS

For the purposes of illustrating the invention, the attached drawings show certain aspects and embodiments that are presently preferred. However, it should be understood that the invention is not limited to the precise methodology or process steps, or system elements as shown in the accompanying drawings.

DETAILED DESCRIPTION OF CERTAIN PREFERRED EMBODIMENTS

An innovative system and methodology for incentivizing patients to comply with the prescription pharmaceutical protocols is disclosed and described through the following several preferred embodiments. A primary element of the system and methodology is the game-style incentive determined by the system and reported to the patient and/or to other caregivers, who may include one or more of doctors, nurses, aids, other patients, and family members. Additional elements of preferred embodiments of the system include the creation of "teams" of patients, or "teams" of patients and caregivers, who are then further incentivized to adhere to their respective protocols, and thereby "help the team." In still further embodiments, the system may incorporate wearable or implanted sensors communicating with variable dispensing devices through a processor, such that the system automatically monitors and reports various important patient metrics, and further uses such metrics to determine whether revisions to the prescription protocol may be warranted.

As described herein, the innovative gamified smart packaging is used to create and transmit a variety of incentives to urge patients to comply with their medication protocols. At its core operating steps, each time a patient dispenses, applies, injects, or otherwise takes his or her medicine, the smart packaging identifies the dispensing or medication event, and transmits a signal to at least one compute devices, such as a smartphone, tablet, or other processor. As defined for this innovation, the smart packaging may be comprised of a pharmaceutical package along with a sensor capable of identifying that a dose of medication has been dispensed or that a dose of medication has been taken. Encompassed in the following embodiments are structures where the sensor is part of the pharmaceutical package or separate from the package.

Upon receiving the signal, an algorithm or app operating on the compute device (or alternatively in the cloud) records the dispensing event, including the time of the event, and reports back to the patient, his or her cumulative "score" of successfully dispensing the medicine. This feedback, and notification of a "score," provides an incentive to the patient to adhere to the prescription protocol, and further provides a basis for the patient to be eligible to receive one or more benefits, including possibly sponsored benefits. Such additional benefits provide a further level of incentives to the patient to maintain compliance.

The software or app operating on one or more compute devices may be programmed to provide various short-term or long-term rewards or benefits as an incentive for the patient to maintain compliance and thereby maximize his score. For example, hitting certain medication dispensing milestones may enable the patient to play an online game, receive an e-book, or receive a discount on various purchases of sponsored products, including for example airline miles, Amazon credits, or possibly pharmacy discounts. In the latter scenario, such pharmacy discounts could be used to reduce the cost of future purchases of the subject medicine.

According to embodiments of the system and methodology, a variety of additional incentives can be provided for attaining various levels of personal or team score. These can come in the non-economic form of recognition through electronic messages, and further or additional economic incentives could be provided through the system by sponsorship of third party organizations—including those with a stake in the user's health (e.g., stores, pharmacies, non-profit organizations focused on various diseases or patient health outcomes).

A series of benefits and rewards could be established that provide increasing incentives as the patient achieves continued or higher "levels" of attainment in order to keep the patient inspired to maintain compliance with the medication protocol. Alternatively, for other patients and situations, upon reaching certain milestones, a simple prompt and congratulatory message or some non-economic benefit may be all that is necessary to incentivize compliance.

A wide array of vendors and sponsors exist who would be interested in gaining access to such clearly defined markets of patients having specific medical conditions and profiles. Such user or patient information can be collected and used in the aggregate without exposing any personal identifiable information, or the identities of any individual patients, thereby ensuring regulatory compliance relating to personal healthcare information.

In another preferred embodiment, patients could be grouped into teams so that their respective individual scores are accumulated into a team score. Studies have shown that in matters of health, people commonly feel a greater responsibility to others than to themselves, especially when the benefits of behavior modification (e.g., taking prescribed medications) are not immediately rewarding (e.g., there is no immediate symptom reduction). Additionally, by adding collaboration capabilities to the software or app, team members could prompt and urge their respective teammates to take their medications, thereby providing the additional incentive to the patient/team member to not let the team down. By way of example, the teaming approach has been used effectively in different aspects for groups such as WeightWatchers and various substance abuse 12-step programs.

As provided in the system and methodology, in the event that a scheduled medicine dosage is missed, the software or app can prompt the patient, and/or alert teammates, or one or more permitted caregivers, who may then provide their own prompts to the user either over electronic media such as the patient's smartphone or through in-person communications. While the software and app will, in some embodiments, provide a prompt or reminder to the patient/team member to take his or her next dose of medication, as noted, a personal message or prompt from a teammate is generally more effective to encourage compliance.

Just being a contributing member of a team boosts the patient's incentive to stay on schedule. The system boosts this incentive by giving the team information to assist in collaborating to keep each team member in compliance and on schedule. Patients need not live in geographic proximity to their teammates for the collaboration and incentive system to work. Nonetheless, increased personal contact can create stronger incentives not to let the team down. Also, by supporting collaboration among patients, individual or team competitions can also be established as further incentive to stay in compliance and on schedule.

The creation of patient teams could also be supported by an on-line or website portal that operates in conjunction with the compute device app. The website could further support a user's ability to select team mates based on geographic proximity, age group, gender, pharmaceutical protocol, or other applicable parameters. Further, the system could provide for caregivers to have the capability to create teams among their patients, of course with permission from each of the patients. In an additional embodiment, the caregivers may also be accorded scores based upon their ability and success in fostering pharmaceutical prescription compliance among their patients or team members.

Figure 1:
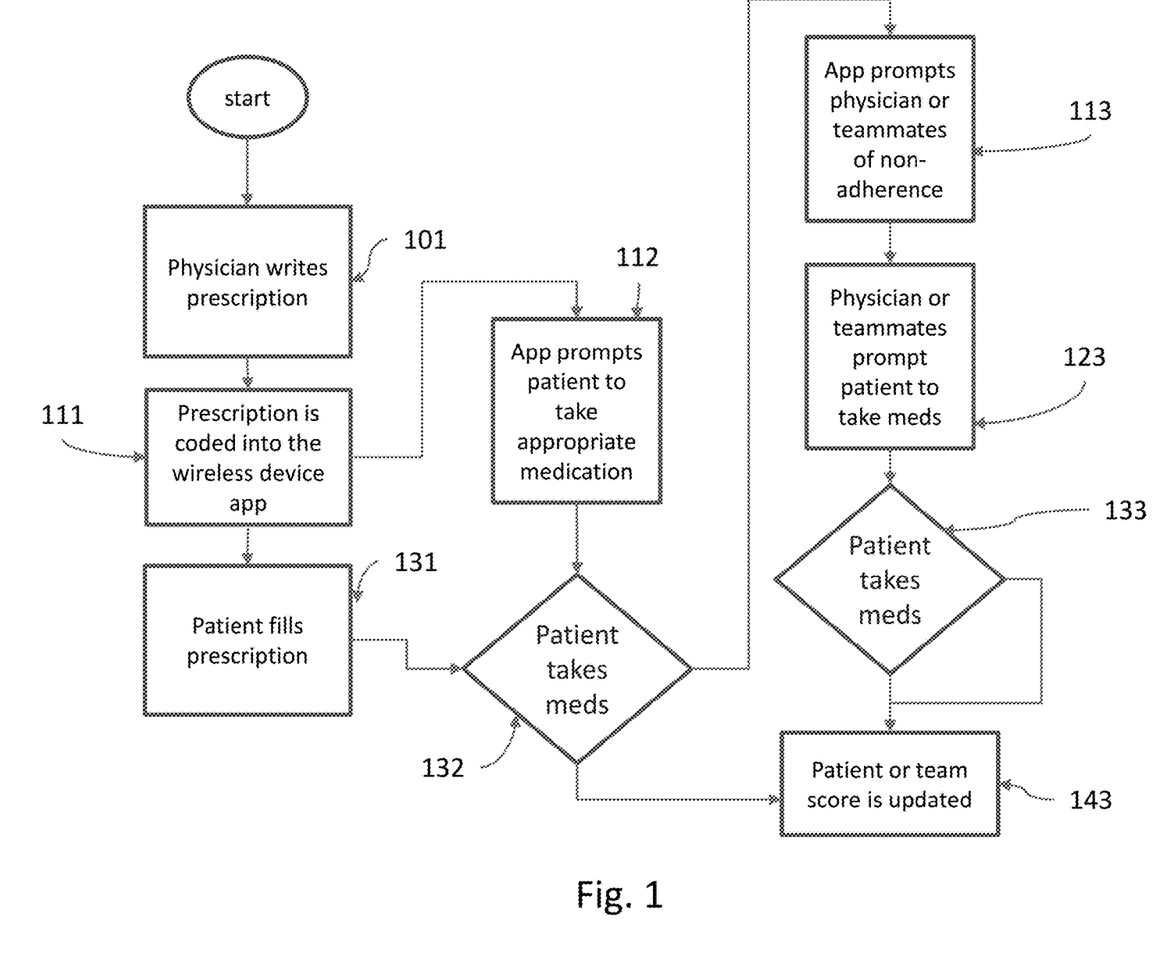
FIG. 1: is a flowchart illustration of an exemplary embodiment of certain methodology steps used within the inventive solution to monitor, track, and incentivize patients to adhere to prescription drug protocols.

FIG. 1 illustrates in a one embodiment, the basic process flow for the innovative gamified pharmaceutical monitoring and dispensing system. In operation, after the physician issues 101 the medication prescription to the patient, the prescription detailed protocol information, including prescription dosage and frequency, is uploaded or transmitted 111 to the patient's compute device and app. In different embodiments the transfer of the prescription protocol may be achieved by the patient, the patient's physician, or through an automated process incorporated into the prescription issuance, including possibly by the patient's insurance carrier.

Next, the patient fills 121 the prescription at the pharmacy or similar vendor. It is important to note that the prescription for the medication must be filled using a form of smart packaging that is capable of identifying and wirelessly reporting each dispensing of the medication, including the time of each medication dispensing.

The system or app automatically monitors when each dosage of the medication is to be dispensed. If the patient does not dispense his or her medication in a timely fashion, and thus the smart packaging does not transmit a dispensing signal to the compute device, then the system or app prompts 112 the patient to take his/her medication in conformance with the prescribed dosage and schedule.

If, on the other hand, the patient timely dispenses 132 the prescribed medication in the correct amount or dosage, then an electronic signal is transmitted from the smart packaging to the system/app which then recalculates or updates the user's score based on the compliance with medication protocol. In certain embodiments, the system algorithms determine an appropriate score based on various data, including timeliness of dose and the accuracy of dosage dispensed by the patient.

As described above, where a "team" of patients is formed, if a patient within a team does not take his or her medication in a timely manner or at the correct dosage, then the system or app is able to prompt 113 one or more team members, or with permission, the prescribing physician of the patient's non-compliance. At this point, the patient's teammates and/or the prescribing physician are in a position to reach out 123 to the patient, and either urge the patient to comply or otherwise attempt to coerce the patient to take his medication.

Should the patient comply and take 133 his medication, an electronic signal is then transmitted to the system or scoring/incentive application. The system accordingly updates 143 the user's score based on the patient's compliance. If, however, the patient does not take his or her medication, the system records 143 such non-compliance, and according does not provide any increased patient or team score. Depending on the rules of the game, it may decrement the individual and/or team score for such non-compliance.

In view of the strict regulatory privacy concerns relating to personal healthcare information, compliance with the prescription pharmaceutical protocol could also be monitored by the doctor with permission from the patient. The system and software have the capability of creating graphical and data driven information relating to patient compliance over time, which could be available for review by the patient and physician at interim visits and annual physicals.

Further, and again with permission, daily reports could be provided to their respective physicians for patients who may need to be placed on a watch list. With such daily or even real-time monitoring, the system provides the physician with the ability to establish criteria whereby the physician is provided automatic alerts or notices of certain critical non-compliance, such as patient A has not taken the prescribed medication for three successive days in a row or patient B has been taking double doses for the past five days.

The innovative system and methodology leverage a variety of currently existing and available smart packaging. Moreover, the system and methodology establish an infrastructure platform which can be further leveraged and scaled to add value and capability for future system enhancements. In one embodiment, local compute devices, being smart phones or laptops could be in direct communication with the smart packaging, and also in communication with one or more remote servers. The remote servers provide further computational capability for enhance analytics, which may be applicable for team competition and large patient group management.

Further, the system could be augmented to accept inputs from biometric, chemical, or other similar sensors used to determine a patient's health (including wearable or implanted sensors) to automatically analyze various physiological data and metrics, and accordingly alter medication dosages or protocols, including schedules. Rather than dispensing a constant or consistent dose in an attempt to maintain levels of bodily parameters (such as blood glucose or red blood cells) or of medication levels (such as antibiotics), medication dosages could be revised based upon real-time sensor readings to provide a more even and more effective dosing.

As to be expected the system is designed to operate seamlessly with available and future wireless communication systems and protocols including Bluetooth, ZigBee, and Z-Wave, other near field communication ("NFC") technologies, but could also be used with dispensers that "plug in" to a base unit that is connected through wiring.

As noted, certain smart packaging currently exists that may be used in conjunction with the innovative methodology and app-based solution. Further, an international standard has been developed for data provided by smart packages, being IEEE STD 11073-10472-2010.

Certain examples of the variety of smart packaging currently on the market include the following:
  GlowCap and GlowPack from Vitality (http://www.vitality.net/products.html)
  Med-ic Smart Label from IMC (http://informationmediary.com/med-ic)• Cerepak from MWV (http://www.mwvaardex.com/Products/DataCollection/Cerepak/index.htm)
  Pharma DDSI Wireless from Stora Enso (http://www.pharmaceuticaltechnlogy.com/features/feature-the-smart-approach-to-pharmapackaging/featurethe-smart-approach-to-pharma-packaging-1.html) Other smart packages may be developed and can readily be used by and incorporated into the inventive system and methodology, including packaging currently being developed for precise dosage metering to support smaller sized pharmaceutical granules. Moreover, the system and methodology may operate in preferred embodiments through use of wearable or implanted sensors that monitor, track and can transmit various patient physiological data and metrics. Such pharmaceutical sensing devices may include sensing of the medication event, which could be a dispensing, taking, ingesting, or applying of the pharmaceutical, as well as the ability to sense and verify that the pharmaceutical has been dispensed, taken, ingested or applied to the appropriate patient. With such sensor technology, patients could be prompted to take the medication more or less frequently based upon the sensed and analyzed metrics in order to better maintain a desired drug impact and health outcome. Alternatively, with such sensor technology and smart dispensing packaging, a regularly medication dosing schedule could be maintained while the solution imposes variations in the dose based upon the metrics monitored, and provided at each prompt. Such variations in dosage or medication timing could be determined to maintain specific levels of bodily constituents or medication levels.

Figure 2:
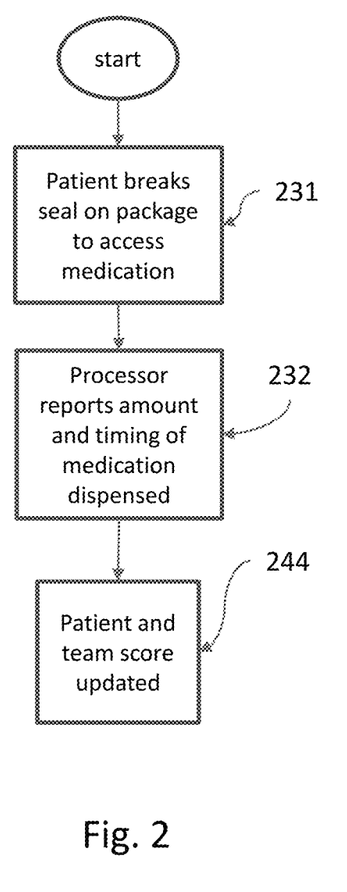
FIG. 2: is a flowchart illustration of an exemplary embodiment of certain methodology steps used whereby smart pharmaceutical packaging identifies and reports prescription adherence.

FIG. 2 shows an exemplary system process flow for the smart package to identify and report prescription adherence. More specifically, the patient opens 231 or breaks a seal, which may be a conductive seal, such as used in medication blister pack). Such action by the patient could alternatively involve tripping a sensor (e.g., interrupting an "electric eye" or engaging a trigger to release the dose) which in turn indicates that that the dose has been dispensed and taken. The system processor records 232 the opening or triggering event, analyzes such event, and transmits information of such event as part of the scoring/incentive application via a communication protocol. The system and app then update 244 the score of the patient and any applicable teams of which the patient is a member.

Figure 3:
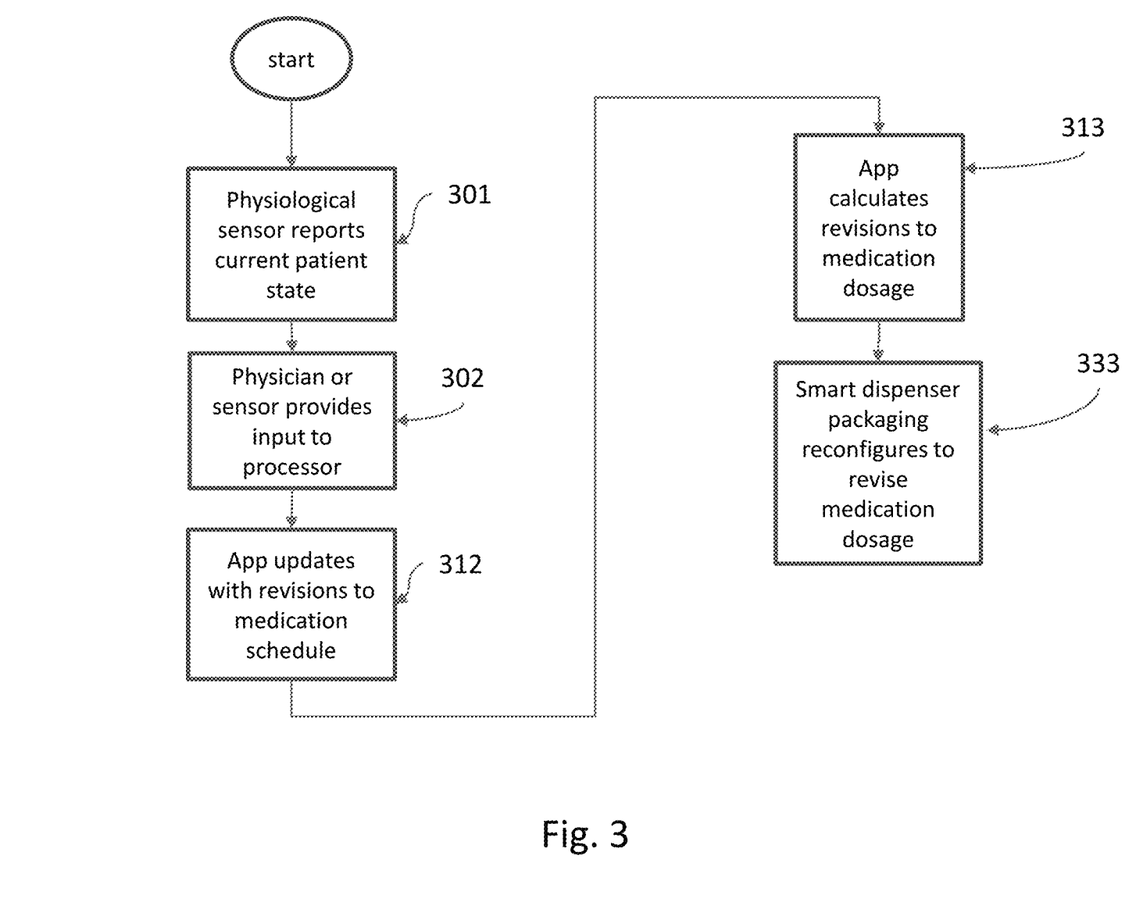
FIG. 3: is a flowchart illustration of an exemplary embodiment of certain methodology steps used by a smart dispenser to identify, analyze, and possibly revise prescription pharmaceutical dispensation.

FIG. 3 shows, in one embodiment a system and process flow for a smart medication dispenser system operation. As described above, this sensor embodiment entails use of at least one sensor that monitors 301 and can transmit signals relating to one or more physiological or environmental metrics relating to the current state of the patient. Such metrics may include (a) the concentration of medication in the bloodstream, or in a particular location in the patient (e.g., in a muscle or particular organ), (b) the level of an internal biological metric (e.g., blood glucose level, white cell count, or heart rate), (c) any other metric relevant to the medication dosage and/or patient condition, or (d) local (to the patient) environment such as temperature, pressure, humidity, brightness, or other conditions. Such sensors may be wearable, implanted, or otherwise remote and external to the patient.

Based on the sensor data, the patient's physician may provide updates 302 to the patient's medication protocol and schedule for dispensing of the pharmaceutical. Alternatively, based upon the sensor data monitored and transmitted, the application may itself automatically calculate 312 any required revision to the dosage schedule. Where the medication change is merely a schedule change (e.g., delaying the next dose), it may be independently updated and completed by the application, by altering the time at which the user is prompted to take the next dose.

If, however, the determined revision requires a change in dosage, the system and application calculate 313 and transmits an instruction to the smart dispenser to alter the dosage to be dispensed to the patient. In response to this instruction, the smart dispenser alters the configuration of dosage 333, and releases or dispenses the new prescribed amount of medication. The smart dispenser may alter and control the dose by mechanisms that include restricting the amount of solid granular or pill medication as well as through altered amounts of liquid medication. This may be accomplished by methods that include altering the size of a receptacle that dispenses the dose, limiting the number of turns of a gear that parse out the medication, limiting the travel of a piston whose travel affects the dosage dispensed, activating a motor for a variable length of time, or other such mechanical dispensing mechanisms.

While preferred embodiments of the inventive methodologies and systems have been described and disclosed, in particular with reference to certain figures and exemplary embodiments of various gamified methodologies to monitor, track, and incentivize patients to adhere to prescription protocols, such exemplary representations are not to be construed as limiting the scope of application of the inventive methodologies or systems. By way of example, the gamification methodologies and systems described herein would have equal application and utility in various non-pharmaceutical environments, including for weight-loss protocols, exercise protocols, stress-relief protocols, and other similar healthcare protocols.

It will be recognized by those skilled in the art that other modifications, substitutions, and/or other applications are possible and such modifications, substitutions, and applications are within the true scope and spirit of the present invention. It is likewise understood that the attached claims are intended to cover all such modifications, substitutions, and/or applications.

What is claimed is:

1. A computerized methodology for recording taking or dispensing of pharmaceuticals using electronic signals from a plurality of smart pharmaceutical packages and monitored contextual information, where said plurality of smart pharmaceutical packages include a sensor and a transmitter, wherein said plurality of smart pharmaceutical packages have a real-time communications link with at least one compute device operating said methodology, and at least one user interface device, wherein said methodology comprises the steps:
   i. loading, by said at least one compute device, a prescription pharmaceutical protocol onto at least one compute device and at least one smart pharmaceutical package, said protocol having an indication of pharmaceutical dosage and related timing for such dosage;
   ii. commencing, by said at least one compute device, a timeline for compliance monitoring for said pharmaceutical protocol;
   iii. monitoring, by said at least one compute device, date and time as compared to said pharmaceutical protocol;
   iv. detecting, by at least one of said plurality of smart pharmaceutical packages, an application, dispensing, injection, ingestion, or other indication of medication taking;
   v. transmitting, by at least one of said plurality of smart pharmaceutical packages, a signal associated with said detecting;
   vi. receiving, by said at least one compute device, a transmission from at least one of said plurality of smart pharmaceutical packages of said signal associated with said detecting;
   vii. recording, by said at least one compute device, said application, dispensing, injection, ingestion, or other indication of medication taking occurrence including the date and time of such occurrence;
   viii. calculating, by said at least one compute device, a current score based upon at least one of: said application, dispensing, injection, ingestion, or other indication of medication taking occurrence; a date and time of said application, dispensing, injection, ingestion, or other indication of medication taking occurrence; a dosage amount of said application, dispensing, injection, ingestion, or other indication of medication taking occurrence; prior system messages; dates, times, sources, and frequency of said prior system messages; and historical and current scores of connected third parties;
   ix. accumulating, by said at least one compute device, said current score with prior calculated scores;
   x. transmitting, by said at least one compute device, a signal relating to said current score and accumulated score to at least one user interface device to report at least one of occurrence of said application, dispensing, injection, ingestion, or other indication of medication taking occurrence, and achieving of said calculated score;
   xi. if a time period lapses without receiving a transmission from said plurality of smart pharmaceutical packages of a possible application, dispensing, injection, ingestion, or other indication of medication taking occurrence, then identifying, by said at least one compute device, a possible non-compliance event;
   xii. recording, by said at least one compute device, said possible non-compliance event; and
   xiii. transmitting, by said at least one compute device, an alerting signal to at least one user interface device of said possible non-compliance event.

2. The computerized methodology for recording taking or dispensing of pharmaceuticals using electronic signals from a plurality of smart pharmaceutical packages and monitored contextual information, as described in claim 1, further comprising at least one of said plurality of smart pharmaceutical packages controlling taking or dispensing of medication and receiving automated instructions directing at least one of an amount of medication to be taken or dispensed, or timing of said taking or dispensing of medication.

3. The computerized methodology for recording taking or dispensing of pharmaceuticals using electronic signals from a plurality of smart pharmaceutical packages and monitored contextual information, as described in claim 1, wherein the calculated current score is modified when the dosage of medication taken or dispensed is different from said pharmaceutical dosage protocol or the timing for medication taken or dispensed is different from said pharmaceutical timing protocol.

4. The computerized methodology for recording taking or dispensing of pharmaceuticals using electronic signals from a plurality of smart pharmaceutical packages and monitored contextual information, as described in claim 1, wherein said alerting signal is modified when the dosage of medication taken or dispensed is different from said pharmaceutical dosage protocol or the timing for medication taken or dispensed is different from said pharmaceutical timing protocol.

5. The computerized methodology for recording taking or dispensing of pharmaceuticals using electronic signals from a plurality of smart pharmaceutical packages and monitored contextual information, as described in claim 1, wherein a reward is issued based on at least one scoring event.

6. The computerized methodology for recording taking or dispensing of pharmaceuticals using electronic signals from a plurality of smart pharmaceutical packages and monitored contextual information, as described in claim 5, wherein said reward is at least one of a monetary reward, a product, a service, an acknowledgement, or an opportunity to play a game.

7. The computerized methodology for recording taking or dispensing of pharmaceuticals using electronic signals from a plurality of smart pharmaceutical packages and monitored contextual information, as described in claim 1, wherein said signal in step (x) is at least one of:
  a. Praise for taking medication;
  b. Encouragement to take medication;
  c. Praise for delaying taking of medication;
  d. Praise for taking less medication than prescribed;
  e. Encouragement to continue to delay taking of medication; and
  f. Encouragement to continue to take less of medication.

8. The computerized methodology for recording taking or dispensing of pharmaceuticals using electronic signals from a plurality of smart pharmaceutical packages and monitored contextual information, as described in claim 1, wherein said at least one user interface device is one of a smartphone, tablet, laptop, computer terminal, display monitor, electronic scoreboard, messaging device, telephone device, paper-tape device, speaker, haptic device, and wearable device.

9. A computerized methodology for recording taking or dispensing of pharmaceuticals using electronic signals from a plurality of smart pharmaceutical packages, monitored contextual information, at least one sensor sensing at least one physiological or environmental metric relating to a pharmaceutical treatment recipient, where said plurality of smart pharmaceutical packages include a sensor and a transmitter, wherein said plurality of smart pharmaceutical packages have a real-time communications link with at least one compute device operating said methodology, and at least one user interface device; wherein said methodology comprises the steps:
  i. loading, by said at least one compute device, a prescription pharmaceutical protocol onto at least one compute device and at least one smart pharmaceutical package, said protocol having an indication of pharmaceutical dosage and related timing for such dosage;
  ii. commencing, by said at least one compute device, a timeline for compliance monitoring for said pharmaceutical protocol;
  iii. monitoring, by said at least one compute device, date and time as compared to said pharmaceutical protocol;
  iv. monitoring, by said at least one compute device, input from said at least one sensor sensing at least one physiological or environmental metric;
  v. transmitting from said at least one compute device to said at least one smart pharmaceutical package a change in the pharmaceutical prescription protocol, based on input from said at least one sensor;
  vi. detecting, by at least one of said plurality of smart pharmaceutical packages, an application, dispensing, injection, ingestion, or other indication of medication taking;
  vii. transmitting, by at least one of said plurality of smart pharmaceutical packages, a signal associated with said detecting;
  viii. receiving, by said at least one compute device, a transmission from at least one of said plurality of smart pharmaceutical packages of said signal associated with said detecting;
  ix. recording, by said at least one compute device, said application, dispensing, injection, ingestion, or other indication of medication taking occurrence including the date and time of such occurrence;
  x. calculating, by said at least one compute device, a current score based upon at least one of: said application, dispensing, injection, ingestion, or other indication of medication taking occurrence; the prescribed time for said application, dispensing, injection, ingestion, or other indication of medication taking occurrence; a date and time of said application, dispensing, injection, ingestion, or other indication of medication taking occurrence; a dosage amount of said application, dispensing, injection, ingestion, or other indication of medication taking occurrence; prior system messages; dates, times, sources, and frequency of said prior system messages; and historical and current scores of connected third parties;
  xi. accumulating, by said at least one compute device, said current score with prior calculated scores;
  xii. transmitting, by said at least one compute device, a signal relating to said current score and accumulated score to at least said at least one user interface device;
  xiii. if a time period lapses without receiving a transmission from said at least one of said plurality of smart pharmaceutical packages of a possible application, dispensing, injection, ingestion, or other indication of medication taking occurrence, then identifying, by said at least one compute device, a possible non-compliance event;
  xiv. recording, by said at least one compute device, said possible non-compliance event; and
  xv. transmitting, by said at least one compute device, an alerting signal to said at least one user interface device of said possible non-compliance event.

10. The computerized methodology for recording taking or dispensing of pharmaceuticals using electronic signals from a plurality of smart pharmaceutical packages, monitored contextual information, as described in claim 9, further comprising, at least one of said plurality of smart pharmaceutical packages controlling taking or dispensing of medication and receiving automated instructions directing at least one of an amount of medication to be taken or dispensed or timing of said taking or dispensing of medication.

11. The computerized methodology for recording taking or dispensing of pharmaceuticals using electronic signals from a plurality of smart pharmaceutical packages and monitored contextual information, as described in claim 9, wherein said signal in step (xii) is at least one of:
  a. Praise for taking medication;
  b. Encouragement to take medication;
  c. Praise for delaying taking of medication;
  d. Praise for taking less medication than prescribed;
  e. Encouragement to continue to delay taking of medication; and
  f. Encouragement to continue to take less of medication.

12. The computerized methodology for recording taking or dispensing of pharmaceuticals using electronic signals from a plurality of smart pharmaceutical packages and monitored contextual information, as described in claim 9, further comprising: identifying at least one team of pharmaceutical treatment recipients; aggregating current scores for said at least one team of pharmaceutical treatment recipients; and providing communications between pharmaceutical treatment recipients within said at least one team of pharmaceutical treatment recipients.

13. The computerized methodology for recording taking or dispensing of pharmaceuticals using electronic signals from a plurality of smart pharmaceutical packages and monitored contextual information, as described in claim 9, wherein said at least one user interface device is one of a smartphone, tablet, laptop, computer terminal, display monitor, electronic scoreboard, messaging device, telephone device, paper-tape device, speaker, haptic device, and wearable device.

14. The computerized methodology for recording taking or dispensing of pharmaceuticals using electronic signals from a plurality of smart pharmaceutical packages and monitored contextual information, as described in claim 12, wherein said teams comprise at least two caregivers selected from pharmaceutical treatment recipients, physicians, nurses, therapists, caregivers, and family members.

15. The computerized methodology for recording taking or dispensing of pharmaceuticals using electronic signals from a plurality of smart pharmaceutical packages and monitored contextual information, as described in claim 9, wherein said at least one sensed physiological or environmental metric is used to revise said prescription pharmaceutical protocol.

16. The computerized methodology for recording taking or dispensing of pharmaceuticals using electronic signals from a plurality of smart pharmaceutical packages and monitored contextual information, as described in claim 9, wherein said at least one sensor is at least one of a wearable sensor, a sub-dermal sensor, an in-body sensor, an external sensor, a remote sensor, a heart rate monitor, a blood pressure monitor, a blood glucose monitor, a chemical concentration monitor, and a white blood count monitor.

17. An automated system for recording taking or dispensing of pharmaceuticals using electronic signals from a plurality of smart pharmaceutical packages and monitored contextual information, said system comprising:
   a. a plurality of smart pharmaceutical packages, each said smart pharmaceutical packages identifying when each pharmaceutical has been dispensed or taken, and transmitting a signal to at least one compute device upon occurrence of each such dispensing or taking event;
   b. at least one sensor sensing at least one physiological or one environmental metric relating to a pharmaceutical recipient following a prescription pharmaceutical protocol;
   c. at least one compute device having a real-time communications link with each of said plurality of smart pharmaceutical packages and having a real-time communications link with said at least one sensor;
   d. at least one user interface device associated with each pharmaceutical recipient, and
   e. a computerized methodology operating within said at least one compute device;
   wherein said computerized methodology comprises the steps:
      i. loading said prescription pharmaceutical protocol onto said at least one compute device, said protocol having an initial indication of pharmaceutical dosage and related timing for said pharmaceutical protocol dosages;
      ii. commencing a timeline for compliance monitoring for said pharmaceutical protocol;
      iii. monitoring date, time, and dosage levels transmitted by the at least one smart package as compared to said pharmaceutical protocol;
      iv. monitoring and recording signals transmitted from said least one sensor; and
      v. based upon analysis of said sensed at least one physiological or environmental metric, revising said pharmaceutical protocol dosage and/or said pharmaceutical protocol dosage schedule within said at least one compute device;
      vi. recording said dispensing or taking event including the date and time of such event;
      vii. calculating a current score based upon at least one of: said dispensing or taking event; a date and time of said dispensing or taking event; a dosage amount of said dispensing or taking event; prior system messages; dates, times, sources, and frequency of said prior system messages; and historical and current scores of connected third parties;
      viii. accumulating said current score with prior calculated scores;
      ix. transmitting said current score and accumulated score to at least said at least one compute device to report the occurrence of said dispensing or taking event and said achieving of said calculated current score;
      x. if a time period lapses without receiving a transmission from said plurality of smart pharmaceutical packages of a dispensing or taking event, then identifying a possible non-compliance event;
      xi. recording said possible non-compliance event; and
      xii. transmitting an alerting signal to said at least one user interface device of said possible non-compliance event.

18. The automated system for recording taking or dispensing of pharmaceuticals using electronic signals from a plurality of smart pharmaceutical packages and monitored contextual information, as described in claim 17, further comprising:
   at least one of said smart pharmaceutical packages capable of receiving automated instructions to control at least one of timing or dosage of medication being taken or dispensed; and wherein based upon analysis of said sensed at least one physiological or environmental metric, said computerized methodology further executes the steps of:
   revising said pharmaceutical protocol dosage and/or said pharmaceutical protocol dosage schedule; and
   transmitting an instruction to said at least one smart pharmaceutical package capable of receiving automated instructions, directing said at least one smart pharmaceutical package capable of receiving automated instructions to revise timing or dosage of medication being taken or dispensed according to said revised pharmaceutical protocol.

19. The automated system for recording taking or dispensing of pharmaceuticals using electronic signals from a plurality of smart pharmaceutical packages and monitored contextual information, as described in claim 17, wherein a reward is issued based on at least one dispensing or taking event.

20. The automated system for recording taking or dispensing of pharmaceuticals using electronic signals from a plurality of smart pharmaceutical packages and monitored contextual information, as described in claim 19, wherein said reward is at least one of a monetary reward, a product, a service, an acknowledgement, or an opportunity to play a game.

21. The automated system for recording taking or dispensing of pharmaceuticals using electronic signals from a plurality of smart pharmaceutical packages and monitored contextual information, as described in claim 17, wherein said transmission in step (ix) further comprises at least one of:
   a. Praise for taking the pharmaceuticals;
   b. Encouragement to take the pharmaceuticals;
   c. Praise for delaying taking of the pharmaceuticals;
   d. Praise for taking less of the pharmaceuticals than prescribed;
   e. Encouragement to continue to delay taking of the pharmaceuticals; and
   f. Encouragement to continue to take less of the pharmaceuticals.

22. The automated system for recording taking or dispensing of pharmaceuticals using electronic signals from a plurality of smart pharmaceutical packages and monitored contextual information, as described in claim 17, wherein said at least one sensor is at least one of a wearable sensor, a sub-dermal sensor, an in-body sensor, an external sensor, a remote sensor, a heart rate monitor, a blood pressure monitor, a blood glucose monitor, a chemical concentration monitor, and a white blood count monitor.

23. The automated system for recording taking or dispensing of pharmaceuticals using electronic signals from a plurality of smart pharmaceutical packages and monitored contextual information, as described in claim 17, wherein said at least one user interface device is one of a smartphone, tablet, laptop, computer terminal, display monitor, electronic scoreboard, messaging device, telephone device, paper-tape device, speaker, haptic device, and wearable device.

* * * * *